United States Patent
Diju et al.

(10) Patent No.: US 12,089,934 B2
(45) Date of Patent: *Sep. 17, 2024

(54) VIBRATING TOURNIQUET AND METHODS OF COLLECTING BLOOD USING SAME

(71) Applicant: Paulus Holdings Limited, Dun Laoghaire (IE)

(72) Inventors: Taufeeq Elahi Diju, Dublin (IE); Ronan Ryan, Glenageary (IE)

(73) Assignee: Paulus Holdings Limited, Dun Laoghaire (IE)

( * ) Notice: Subject to any disclaimer, the term of this patent is extended or adjusted under 35 U.S.C. 154(b) by 772 days.

This patent is subject to a terminal disclaimer.

(21) Appl. No.: 17/080,269

(22) Filed: Oct. 26, 2020

(65) Prior Publication Data

US 2021/0038139 A1 Feb. 11, 2021

Related U.S. Application Data

(63) Continuation of application No. 16/775,889, filed on Jan. 29, 2020, now Pat. No. 10,888,258, which is a (Continued)

(51) Int. Cl.
*A61B 17/132* (2006.01)
*A61B 5/15* (2006.01)

(52) U.S. Cl.
CPC ...... *A61B 5/150083* (2013.01); *A61B 17/132* (2013.01)

(58) Field of Classification Search
CPC ........ A61B 5/150022; A61B 5/150053; A61B 5/150083; A61B 5/150137; A61B 5/6824;
(Continued)

(56) References Cited

U.S. PATENT DOCUMENTS 4,887,594 A * 12/1989 Siegel .................. A61M 35/10
601/72
6,203,509 B1 3/2001 Duboff
(Continued)

FOREIGN PATENT DOCUMENTS

| WO | WO-2009081405 A2 | 7/2009 |
| WO | WO-2016178952 A1 | 11/2016 |
| WO | WO-2019010008 A1 | 1/2019 |

OTHER PUBLICATIONS

Baxter, et al., "An Integration of Vibration and Cold Relieves Venipuncture Pain in a Pediatric Emergency Department," <https://www.ncbi.nlm.nih.gov/pubmed/22134226> Pediatric Emergency Care, vol. 27, No. 12, Dec. 2011, pp. 1151-1156.

(Continued)

*Primary Examiner* — Darwin P Erezo
*Assistant Examiner* — Christian D Knauss
(74) *Attorney, Agent, or Firm* — Goodwin Procter LLP

(57) ABSTRACT

A device and method for collecting blood from an anatomical feature of a mammalian subject, the device including a vibrating plate assembly structured and arranged to retain the anatomical feature, a first biasing device releasably attachable to the vibrating plate assembly, a housing portion releasably connectable to the vibrating plate assembly, and a plurality of vibrating motors located beneath the vibrating plate assembly, such that vibrations translated to the anatomical feature enhance blood collection, such that the first biasing device constricts blood flow to the collection point on the anatomical feature, causing blood to pool therein, and low frequency and/or high amplitude vibrations cause vasodilation, encouraging blood flow through the capillaries at the collection point.

18 Claims, 11 Drawing Sheets

Related U.S. Application Data continuation-in-part of application No. 16/359,186, filed on Mar. 20, 2019, now Pat. No. 10,610,142.

(58) Field of Classification Search
CPC ..... A61B 5/6825; A61B 5/6826; A61B 17/12; A61B 17/132; A61B 2017/00438; A61B 2017/0042; A61B 2017/00442; A61F 5/41; A61F 5/05866; A61F 5/05875; A61H 23/00; A61H 19/00; A61H 19/3032; A61H 19/34; A61H 19/50; A61H 11/00; A61M 5/42; A61M 5/422; A61M 5/425

See application file for complete search history.

(56) References Cited

U.S. PATENT DOCUMENTS

| | | | |
|---|---|---|---|
| 8,206,336 B2 | 6/2012 | Shantha | |
| 9,333,144 B2 | 5/2016 | Baxter et al. | |
| 9,463,026 B2 | 10/2016 | Corrigan, Jr. | |
| 10,888,258 B2 * | 1/2021 | Diju | A61B 5/150946 |
| 2003/0181835 A1 | 9/2003 | Klein | |
| 2003/0220663 A1 | 11/2003 | Fletcher et al. | |
| 2004/0020241 A1 | 2/2004 | Boiadjian | |
| 2004/0046678 A1 * | 3/2004 | Grady, Jr. | B60Q 7/00 340/815.45 |
| 2006/0247493 A1 * | 11/2006 | Chen | A61F 6/04 600/38 |
| 2007/0083131 A1 | 4/2007 | Escutia et al. | |
| 2007/0088385 A1 | 4/2007 | Perry | |
| 2009/0012355 A1 * | 1/2009 | Lin | A61H 19/34 600/38 |
| 2009/0177224 A1 | 7/2009 | Naghavi et al. | |
| 2009/0306468 A1 | 12/2009 | Tasker et al. | |
| 2010/0004518 A1 * | 1/2010 | Vo | A61B 5/6843 165/185 |
| 2010/0179457 A1 | 7/2010 | Blaine et al. | |
| 2011/0118568 A1 | 5/2011 | Sei | |
| 2011/0166498 A1 | 7/2011 | Shantha | |
| 2012/0184884 A1 | 7/2012 | Dyer et al. | |
| 2012/0203141 A1 | 8/2012 | Shantha et al. | |
| 2013/0109914 A1 | 5/2013 | Imboden et al. | |
| 2015/0257970 A1 | 9/2015 | Mucke et al. | |
| 2018/0369064 A1 * | 12/2018 | Baxter | A61F 7/02 |
| 2019/0091598 A1 | 3/2019 | Milanesi et al. | |
| 2019/0099117 A1 * | 4/2019 | Pulitzer | A61B 5/150137 |
| 2020/0297260 A1 | 9/2020 | Diju et al. | |

OTHER PUBLICATIONS

Inal, et al., "Relief of Pain During Blood Specimen Collection in Pediatric Patients" The American Journal of Maternal/Child Nursing, Abstract, (2012), vol. 37, No. 5, 2 pages.
International Search Report and Written Opinion in PCT/IB2019/000271, dated Dec. 19, 2019 12 pages.
International Search Report and Written Opinion in PCT/IB2020/000199, dated Sep. 10, 2020 13 pages.
Preliminary Rejection for Korean Patent Application No. 10-2021-7033359 dated Oct. 15, 2021.

* cited by examiner

VIBRATING TOURNIQUET AND METHODS OF COLLECTING BLOOD USING SAME

CROSS-REFERENCE TO RELATED APPLICATIONS

This application is a continuation of and claims priority to and the benefit of U.S. patent application Ser. No. 16/775,889, filed Jan. 29, 2020, which is a continuation-in-part of U.S. patent application Ser. No. 16/359,186 filed on Mar. 20, 2019 (now U.S. Pat. No. 10,610,142), the disclosures of which are incorporated herein by reference in their entireties.

FIELD OF INVENTION

Devices and methods for collecting blood from a mammalian digit and, more particularly, a vibrating tourniquet for collecting capillary blood from the digit, as well as methods for doing the same are described.

BACKGROUND OF INVENTION

Conventionally, for venous blood collection, a tourniquet may be placed tightly around some portion of an extremity, typically between the subject's heart and the location from which the blood sample is collected or drawn. For example, when drawing blood from the subject's forearm, a tourniquet (e.g., an elastic band) may be placed around the subject's upper arm. The tourniquet restricts the flow of blood to the sampling or drawing location and also makes the veins inside the subject's elbow more pronounced and easier to find and to puncture with a needle.

A similar device does not exist for capillary blood collection, for example from the subject's finger. Typically, finger tourniquets have been used to stop blood flow entirely but not to restrict the flow of blood to the end of the digit where a blood sample is usually collected. Very small volumes of blood (e.g., about 150 µl) may be drawn without using a tourniquet (e.g., using a capillary pipette), but larger volumes of blood are generally not sampled from a subject's fingertip.

Taking a blood sample from a subject's finger using capillary blood collection techniques can also be challenging due to dozens of variables that might reduce capillary blood flow. For example, dehydration, fatigue, lack of exercise, cold weather, and cold hands may reduce blood flow to the collection site. Circulatory disorders, resulting from, for example, obesity, diabetes mellitus, arthritis, disability, heart conditions, and arterial issues, may also cause reduced blood flow to peripheral regions, such as the subject's hands or feet.

BRIEF SUMMARY OF THE INVENTION

Accordingly, it would be desirable to provide a device and method for collecting capillary blood from a mammalian digit (e.g., a human finger) that increase the volume of blood proximate or in the vicinity of the point of blood collection and that, furthermore, encourage blood to flow in the capillaries during the drawing process.

In a first aspect, some embodiments of the present invention include a device for collecting blood from a mammalian digit. In some implementations, the device may include a rigid cradle portion structured and arranged to retain the digit, a first biasing device releasably attachable to the cradle portion and structured and arranged to constrict blood flow in the digit, a housing portion releasably connectable to the cradle portion, and a plurality of vibrating motors located beneath the cradle portion within the housing portion, such that vibrations translated to the digit enhance blood flow. In some variations, the cradle portion may be a vibrating plate that includes a plurality of ribs, while the first biasing device may be any one of an elastic device, an elastic band, a rubber device, a rubber band, and/or a hook and pile combination.

In some applications, the device also may include one or more of the following: a power source(s) (e.g., a battery), a second biasing device (e.g., a spring) located in the housing portion and structured and arranged to bias the vibrating motors against the cradle portion, and/or a processing device adapted to combine vibrations waves from each of the vibrating motors to produce the resulting low frequency wave. In some embodiments, each of the vibrating motors may include a shaft and a weight that is located off center from the shaft, so that the off center weight produces vibration that, in some variations, may be combined to provide a resulting wave characterized as having a low frequency.

In a second aspect, some embodiments of the present invention involve a method of collecting capillary blood from a mammalian digit. In some implementations, the method may include providing a tourniquet device to constrict blood flow in the digit, wherein the tourniquet device may include a rigid cradle portion structured and arranged to retain the digit, a first biasing device (e.g., elastic device, an elastic band, a rubber device, and a rubber band) releasably attachable to the cradle portion, a housing portion releasably connectable to the cradle portion, and a plurality of vibrating motors located beneath the cradle portion within the housing portion. The method may further include: positioning the first biasing device over the digit retained in the cradle portion; releasably attaching the first biasing device to the cradle portion to constrict blood flow in the digit; and producing vibrations by the vibrating motors, such that the vibrations translate to the digit retained in the cradle portion, thereby increasing blood flow into capillaries in the digit for collection.

In some applications, the method may also include controlling the vibrating motors to produce vibrations having a low frequency and/or a high amplitude. In some variations, vibration waves having a high frequency and a high amplitude may be produced by each vibrating motor and, furthermore, these high frequency vibrations may be combined to create a resultant low frequency output.

In a third aspect, the present invention relates to a device for collecting blood from an anatomical feature of a mammalian subject. In some embodiments, the device includes a rigid vibrating plate assembly structured and arranged to push against the anatomical feature from which blood is collected; a housing portion releasably connectable to the vibrating plate assembly; a first biasing device (e.g., elastic device, an elastic band, a rubber device, a rubber band, and a hook and pile combination) attached to the housing portion and releasably attachable to the vibrating plate assembly, wherein the first biasing device is structured and arranged to constrict blood flow in the anatomical feature; and vibrating motors located beneath the vibrating plate assembly, wherein vibrations generated by the vibrating motors enhance blood flow in and to the anatomical feature.

In some variations, the first biasing device may include and/or the vibrating plate assembly may include a number of ribs for providing traction and/or several quick connect projections for releasably attaching the vibrating plate assembly to the housing portion. In some applications, the quick connect projections are configured to mate with corresponding openings formed in the housing portion.

In some variations, the device may also include one or more of the following: a power source(s) (e.g., a battery), a post portion fixedly attached to the vibrating plate assembly, and a second biasing device (e.g., a spring) disposed about the post portion and structured and arranged to bias the vibrating motors against the vibrating plate assembly, a leaf spring mechanism (e.g., an S-shaped mechanism) that is structured and arranged to provide an auto-start condition when the leaf spring mechanism is compressed, and/or a printed circuit board that is releasably attachable to the vibrating plate assembly. In some variations, the second biasing device may be structured and arranged to push the vibrating plate assembly against the anatomical feature. In some implementations, the printed circuit board may include an opening through which a post portion extends and the leaf spring mechanism is fixedly attached to a bottom surface of the printed circuit board.

In a fourth aspect, the present invention relates to a method of collecting capillary blood from an anatomical feature of a mammalian subject. In some embodiments, the method includes: providing a tourniquet device to constrict blood flow in the anatomical feature, wherein the tourniquet device may include a rigid vibrating plate assembly structured and arranged to push against the anatomical feature from which blood is collected, a housing portion releasably connectable to the vibrating plate assembly, a first biasing device attached to the housing portion and releasably attachable to the vibrating plate assembly, wherein the first biasing device is structured and arranged to constrict blood flow in the anatomical feature, and several vibrating motors located beneath the vibrating plate assembly, wherein vibrations generated by the vibrating motors enhance blood flow in and to the anatomical feature; positioning the first biasing device over the anatomical feature retained in the vibrating plate assembly; releasably attaching the first biasing device to the vibrating plate assembly to constrict blood flow in the anatomical feature; and producing vibrations by the vibrating motors, such that the vibrations translate to the anatomical feature retained in the vibrating plate assembly, thereby increasing blood flow into the capillaries in the anatomical feature for collection.

BRIEF DESCRIPTION OF DRAWINGS

Various features and advantages of the present invention, as well as the invention itself, can be more fully understood from the following description of the various embodiments, when read together with the accompanying drawings, in which.

DETAILED DESCRIPTION OF THE INVENTION

Figure 1:
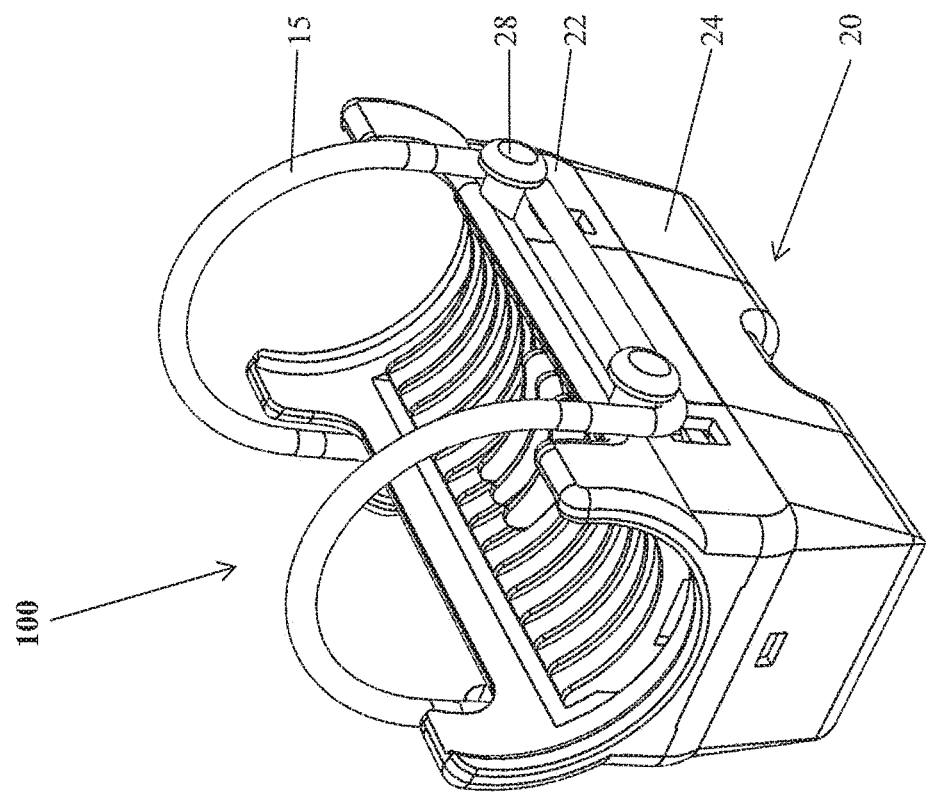
FIG. 1 shows a top perspective view of a device for collecting blood, in accordance with some embodiments of the present invention.

Although the invention will be described in an application for collecting blood from a human fingertip, those of ordinary skill in the art can appreciate that the device and method described herein may be applied to any digit (e.g., toes and fingers) or other appendage of a mammalian subject.

Vibrating Tourniquet for Collecting Blood

Referring to FIGS. 1 through 4, an illustrative embodiment of a vibrating tourniquet for collecting capillary blood from a human digit is shown. In some implementations, the device 100 includes an upper (cradle) portion 10, a biasing element 15, and a lower (housing) portion 20 that are each structured and arranged to accommodate a human finger for the purpose of collecting capillary blood. In some applications, the cradle portion 10 may include an arcuate-shaped substrate 12 made of plastic, metal, or a combination thereof and having a proximal end 14 and a distal end 16. Preferably, the arcuate-shaped substrate 12 is adapted and dimensioned to accommodate all or some portion of a human digit.

In some variations, a vibrating plate 11 includes a plurality of ribs. The ribbed, vibrating plate 11 may provide an interface between the human skin and the vibratory motors. In some variations, the ribbed, vibrating plate 11 is translatable, so that the ribbed, vibrating plate 11 is able to conduct vibrations from vibratory motors to the subject's digit. Moreover, the vibrating plate 11 is ribbed to create greater friction against the skin of the digit. For example, the individual ribs of the ribbed, vibrating plate 11 may be oriented normal, perpendicular, or substantially perpendicular to the longitudinal axis of the cradle portion 10. The ribs of the vibrating plate 11 support and contact portions of the digit, ensuring that the portions of the digit are in and remain in communication with the ribbed, vibrating plate 11. Although the vibrating plate 11 of the present invention is described as being ribbed, those of ordinary skill in the art can appreciate that other patterns and/or textures could be used as an alternative.

Figure 2:
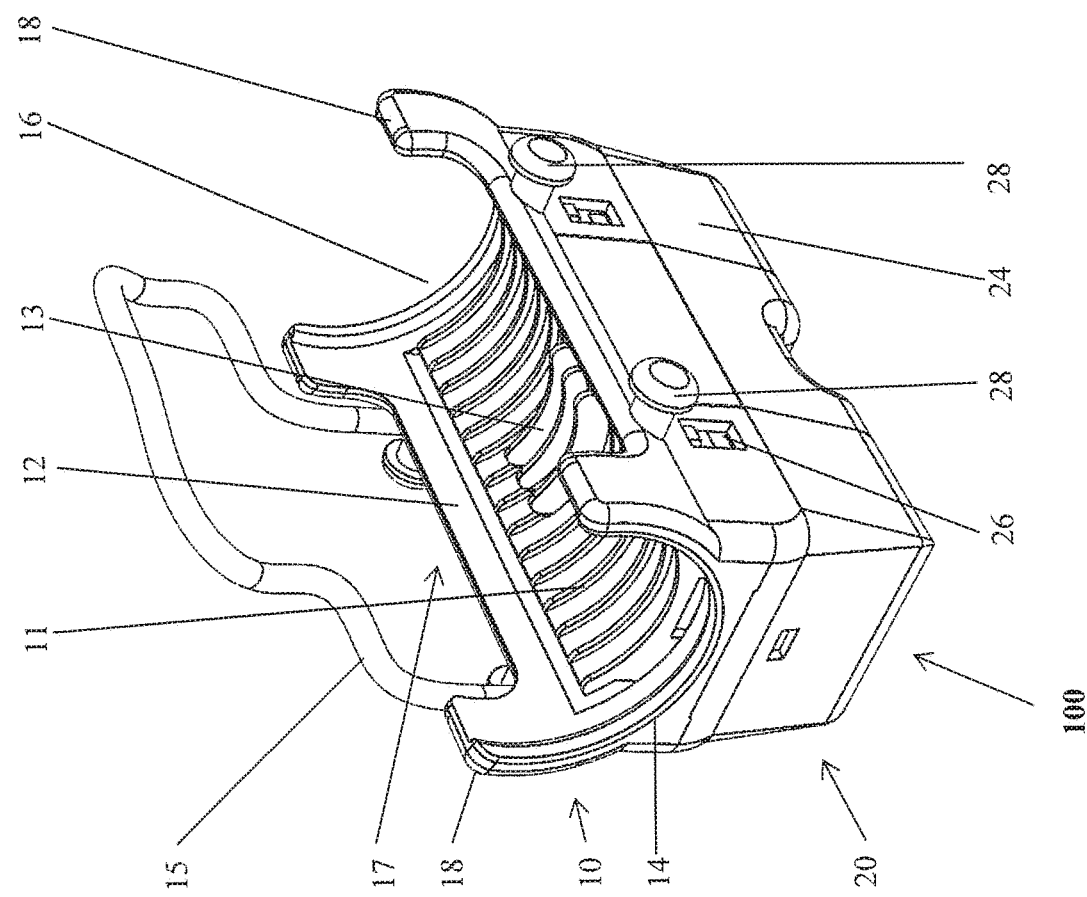
FIG. 2 shows a top perspective view of the device of FIG. 1 with the biasing element attached to each of the attachment posts, in accordance with some embodiments of the present invention.
Figure 4:
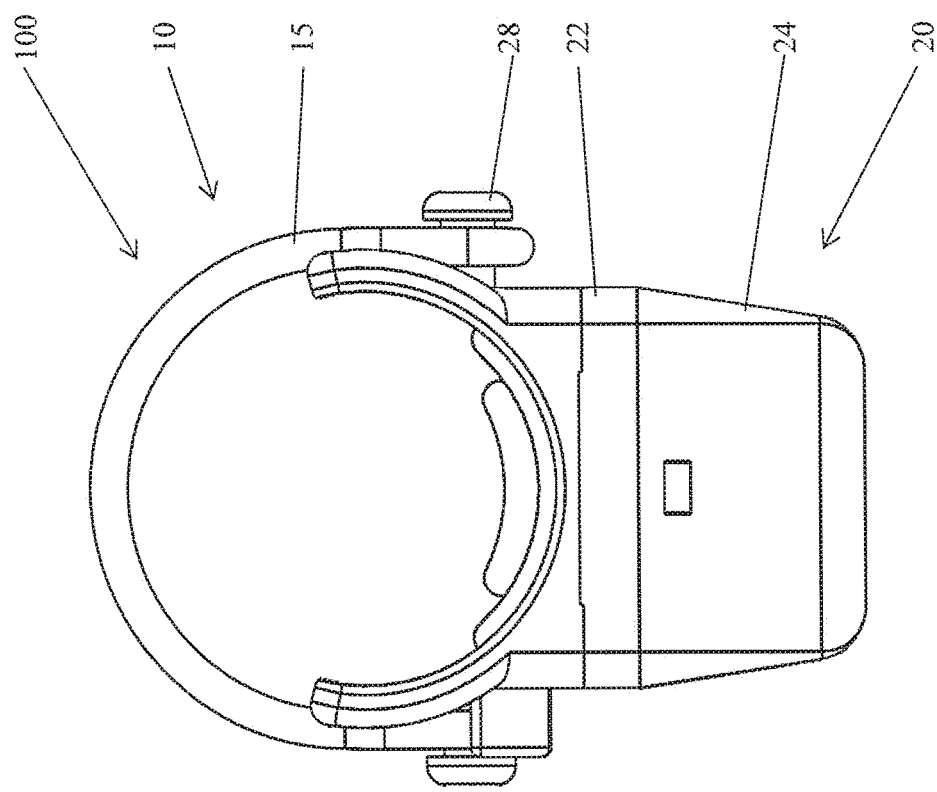
FIG. 4 shows a front view of the device of FIG. 2, in accordance with some embodiments of the present invention.
Figure 3:
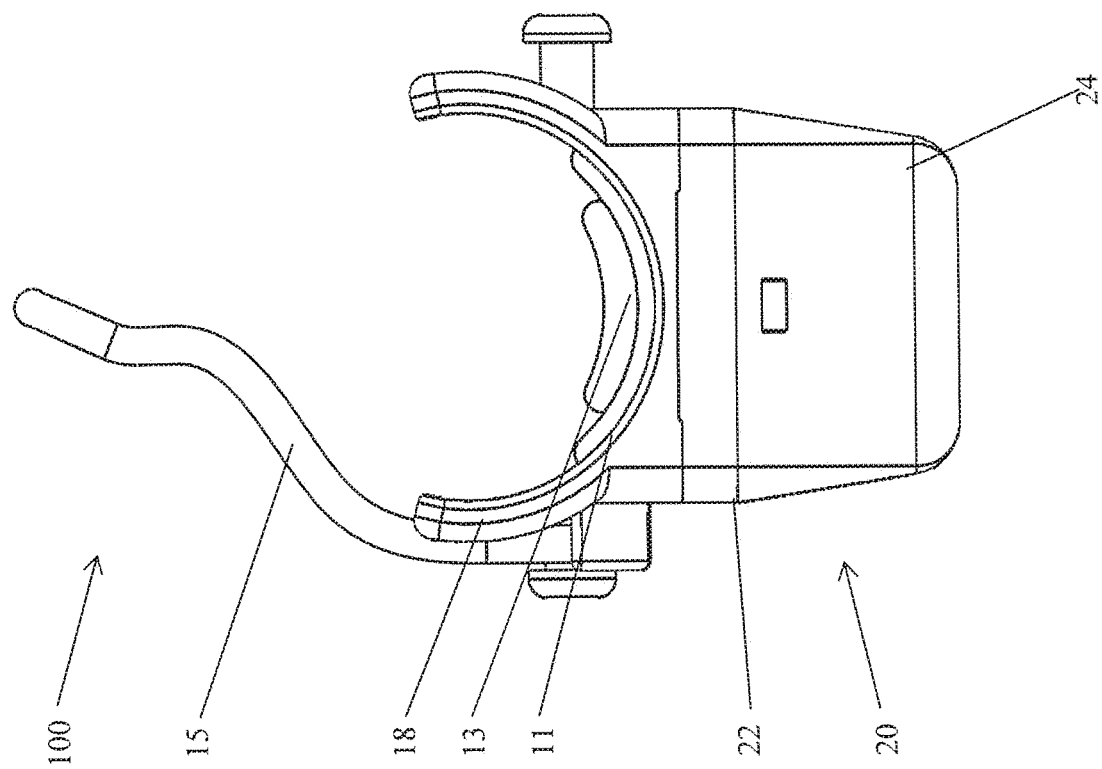
FIG. 3 shows a front view of the device of FIG. 1, in accordance with some embodiments of the present invention.

Optionally, to provide an auto-start capability to turn on the device 100 without having to turn on the device 100 manually, an extended rib portion 13 may be provided through the ribbed, vibrating plate 11. As shown in FIGS. 1 and 2, the extended rib portion 13 may be located within the invert of the arcuate-shaped substrate 12 and, more particularly, the extended rib portion 13 may be located within an opening in the vibrating plate 11 provided therefor. In some variations of the cradle portion 10, when a digit is placed within the device 100, the middle phalanx and/or the proximal phalanx of a finger may cover and contact the extended rib portion 13. Also, as shown in FIGS. 1 and 2, the ribs in the extended rib portion 13 project above the ribs in the vibrating plate 11. This feature ensures that, when a digit is placed in the cradle portion 12, the digit contacts the extended rib portion 13, which will automatically turn on the device 100. More specifically, once the digit contacts the extended rib portion 13, the force applied by the digit on the extended rib portion 13 will force the extended rib portion 13 down, through the opening in the vibrating plate 11. The extended rib portion 13 depresses an ON/OFF button that may be located on a printed circuit board located beneath the vibrating plate 11.

In some applications, projections 18 extend at both ends 14, 16 of and from both sides of the arcuate-shaped substrate 12, so as to produce open sections 17 on both sides of the arcuate-shaped substrate 12. The open sections 17 provide a space for looping the biasing element 15 (e.g., an elastic device, an elastic band, a rubber device, a rubber band, a hook and pile combination, and the like) over the digit, ensuring that the biasing element 15 remains in intimate contact with the digit, so that the biasing element 15 constricts the flow of blood to the fingertip.

In some embodiments, the housing portion 20 may include an upper portion 22 and a lower portion 24. In some variations, the lower portion 24 may be releasably connectable to the upper portion 22 using one or more connecting devices 26 that may be disposed on opposing sides of the housing portion 20. For example, a set (e.g., a pair) of attachment posts 28 may also be fixedly attached on opposing sides of the upper portion 22 of the housing portion 20. In operation, in order to maintain intimate contact between the digit and the biasing element 15 and to ensure that the biasing element 15 constricts the flow of blood to the fingertip, the biasing element 15 may be looped around each of the attachment posts 28 on both sides of the housing portion 20 to place the biasing element 15 in tension. If the biasing element 15 is, in the alternative, a hook and pile combination, a bar may be fixedly attached between the attachment posts 28 on each side of the upper portion 22 of the housing portion 20, such that there is a space formed between the bar and the upper portion 22 of the housing portion 20. One end of the hook and pile combination may be securely attached around the bar on one side of the upper portion. In order to constrict the flow of blood to the fingertip, the free-running end of the hook and pile combination may be inserted in the space between the bar and the upper portion 21 of the housing portion 20; pulled tightly back onto itself to apply pressure to the digit in the cradle portion 12; and the hook portion and pile portion may be brought into contact with one another to maintain the pressure on the digit.

Additional components of the device 100 may be located within the housing portion 20. For example, referring to FIG. 5, the housing portion 20 may include a number of plenum spaces 51, 52, 53. In some implementations, one or more of the plenum spaces 51, 52 may be dimensioned and configured to accommodate a power source 54 (e.g., one or more DC battery), while other plenum space 53 may be dimensioned and configured to accommodate a printed circuit board (PCB) 55, as well as a plurality of (e.g., two) vibrating motors 56a, 56b. Preferably, the vibrating motors 56a, 56b are fixedly attached to the PCB 55 and the PCB 55 is fixedly attached to the ribbed, vibrating plate 11, so that, in operation, the vibrating motors 56a, 56b cause the PCB 55, the vibrating plate 1, and the digit to vibrate. The spring 58 provides some damping such that a majority of the vibrations are carried to the vibrating plate 11 and the finger and very little of the vibrations is directed towards other parts of the device 100.

An ON/OFF button 57 may be provided on the PCB 55, while a second biasing element 58 (e.g., a spring) may be disposed against the underside of the PCB 55. Although an extending rib portion 13 and an ON/OFF button 57 may be provided to provide an auto-start capability, in some variations a conventional ON/OFF switch (e.g., a slider switch, a push switch, and the like) may be provided on exterior of the housing 20.

In some variations, the PCB 55 may include a processing device (e.g., a microprocessor unit) that is capable of executing a software program, algorithm, driver program and the like stored in memory. In some embodiments, the software program, algorithm, driver program and the like may be adapted to control the frequency and/or amplitude of the vibrations produced by each motor 56a, 56b, thereby defining the final beating frequency output. The PCB 55 may also include other hardware and/or software for driving the motors 56a, 56b, voltage regulators, and other circuit protection components on the PCB 55.

Figure 5:
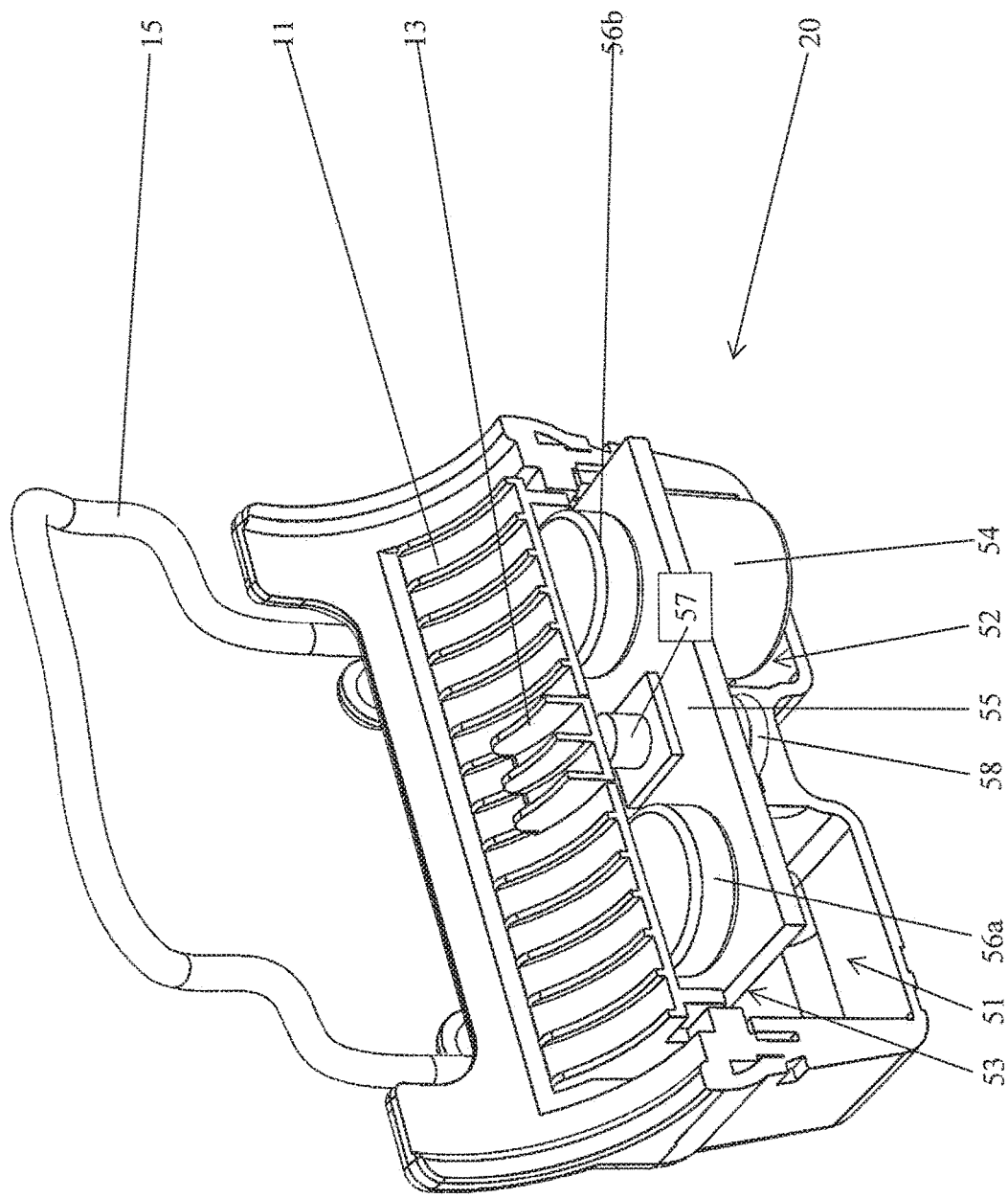
FIG. 5 shows a cross sectional view of the device of FIG. 1, in accordance with some embodiments of the present invention.

As shown in FIG. 5, the extended rib portion 13 and ribbed, vibrating plate 11 may be configured to translate freely up and down within the arcuate-shaped substrate 12 of the cradle portion 10. As a result, once a digit is placed against the extended rib portion 13, the extended rib portion 13 is structured and arranged to displace (e.g., in a downward direction) with respect to the vibrating plate 11, further depressing the ON/OFF button 57 sufficiently to turn on the PCB 55 and/or cause the PCB 55 to execute a start-up program. Moreover, as the digit is further pushed into the cradle portion 10, force from the digit may cause the ribbed, vibrating plate 11 to displace (e.g., in a downward direction) with respect to the arcuate-shaped substrate 12 of the cradle portion 10. Such displacement of the ribbed, vibrating plate 11 will also force the PCB 55 down against the spring 58.

The spring 58 may be adapted to ensure that, during vibration, the vibrating motors 56a, 56b stay in intimate contact with the ribbed, vibrating plate 11 and, moreover, that the ribbed, vibrating plate 11 remains in intimate contact with the digit in the cradle portion 10. There can be a single spring 58 (as shown) or multiple springs 58 used in the device 100. In operation, once the biasing element 15 exerts pressure onto the digit, the translating vibrating plate 11 compresses both the ON/OFF switch 57 and the spring 58. The spring constant in the spring 58 will tend to resist this compressive force, causing the spring 58 to push the PCB 55, the vibrating motors 56a, 56b, and the ribbed, vibrating plate 11 against the skin of the digit. This spring-loaded mechanism ensures that the resistive force with which the ribbed, vibratory plate 11 is pressed against the digit is governed by the force of the spring 58 and not by how tightly the device 100 has been tightened around the finger using the biasing element 15. This prevents overtightening of the ribbed, vibratory plate 11 against the skin of the digit, which could lead to total cut-off of blood supplied to the finger.

Figure 6:
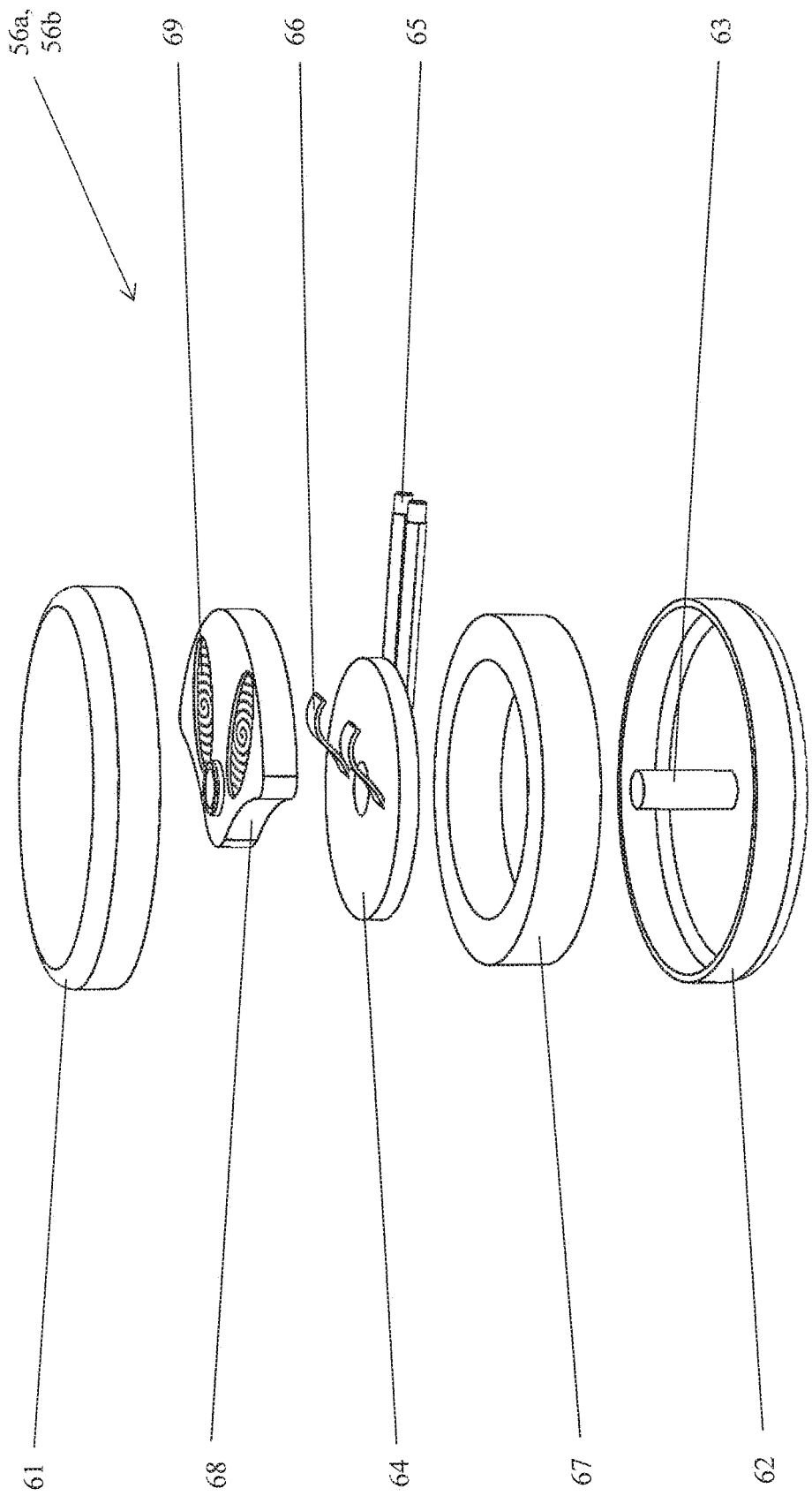
FIG. 6 shows an exploded view of a coin-type vibrating motor, in accordance with some embodiments of the present invention.

In some embodiments, once the PCB 55 and device 100 have started up properly, the PCB 55 may include one or more software programs, algorithms, driver programs, and the like to cause the plurality of vibrating motors 56a, 56b to generate vibrations in a desired manner and fashion. More particularly, it may be desirable for the vibrating motors 56a, 56b to generate vibrations in a beating phenomenon or at a beating frequency. An exemplary, coin-type vibrating motor 56a, 56b suitable for use with the device 100 is shown in FIG. 6. In some embodiments, the vibrating motors 56a, 56b may include an upper casing 61 and a lower casing 62, the lower casing including a shaft 63. A substrate 64 that includes a printed circuit board may be configured to include an opening adapted to fit over the shaft 63. Power for running the motors 56a, 56b may be provided to components on the substrate via an electrical bus on the PCB 55 or, in the alternative, power may be provided directly from the power source 54, e.g., via electrical leads 65 from the power source 54 to the motors 56a, 56b. A pair of brushes 66 may be located on the substrate 64. A magnet 67 may be adapted to surround the brushes 66. An imbalanced weight 68 having a plurality of coil assemblies 69 may be placed over the shaft 63 and atop the magnet 67. In operation, the brushes 66 provide power selectively or alternately to the coil assemblies 69, thereby alternating the direction of a magnetic field induced by current flowing through the coil assemblies 69. The induced magnetic field interacts with the magnetic flux from the magnet 67. The alternating direction of the induced magnetic field and the interaction between the induced magnetic field and the magnetic flux cause the imbalanced weight 68 to rotate about the shaft 63. Due to an off-center mass in the imbalanced weight 68, the rotating imbalanced weight 68 produces wobble and vibrations.

Although the figures show an embodiment that includes two motors 56a, 56b, this is done for illustrative purposes only. Performance may further be improved by using more than two motors 56a, 56b to enhance the beating effect. In some instances, it may also be possible to produce a desired beating phenomenon use a single motor having a mechanism coupled to the motor's shaft. Such an arrangement would work more like a car's gearbox, which increases or reduced the output speed and torque mechanically rather than electronically.

Referring to FIGS. 10A through 12, an illustrative second embodiment of a vibrating tourniquet for collecting capillary blood is shown. In some implementations, the device 100' includes an upper portion 10', a first biasing element 15', and a lower portion 20' that are each structured and arranged to accommodate some portion of a human being (e.g., a digit, a finger, a toe, an appendage, a foot, a hand, and the like) for the purpose of collecting capillary blood. In some applications, the upper portion 10' may include a vibrating plate assembly 70 that, in some applications, may be made of plastic, metal, or a combination thereof. Preferably, the vibrating plate assembly 70 provides an arcuate-shaped structure that is adapted and dimensioned to accommodate all or some portion of a human digit, appendage, foot, hand, and the like.

Optionally, in some applications, the vibrating plate assembly 70 may include a plurality of ribs 71 that may be structured and arranged to provide greater traction against the skin of the digit, appendage, foot, or other portion of the human body inserted into the device 100'. The ribs 71 of the vibrating plate assembly 70 support and contact portions of the digit, appendage, foot, or other portion of the human body inserted into the device 100', ensuring that the digit, appendage, foot, or other portion of the human body inserted into the device 100' are in and remain in physical contact with the vibrating plate assembly 70. In some variations, the individual ribs 71 of the vibrating plate assembly 70 may be oriented normal, perpendicular, or substantially perpendicular to the longitudinal axis of the upper portion 10'. Although the vibrating plate assembly 70 of the present invention is shown and described as being ribbed, those of ordinary skill in the art can appreciate that other patterns and/or textures could be used as an alternative for providing traction between the portion of the human body inserted into the device 100' and the vibrating plate assembly 70 of the device 100'.

The vibrating plate assembly 70—whether ribbed or not—is configured to provide an interface between the human skin and the vibratory motors 56a', 56b'. Advantageously, the vibrating plate assembly 70 is translatable, so that, when compressed, the vibrating plate assembly 70 provides a self-starting or auto-start feature, while also ensuring that the vibrating plate assembly 70 is able to conduct vibrations generated or produced by a plurality of vibratory motors 56a', 56b' to the portion of the subject's or patient's body contained within the device 100'.

Figure 10A:
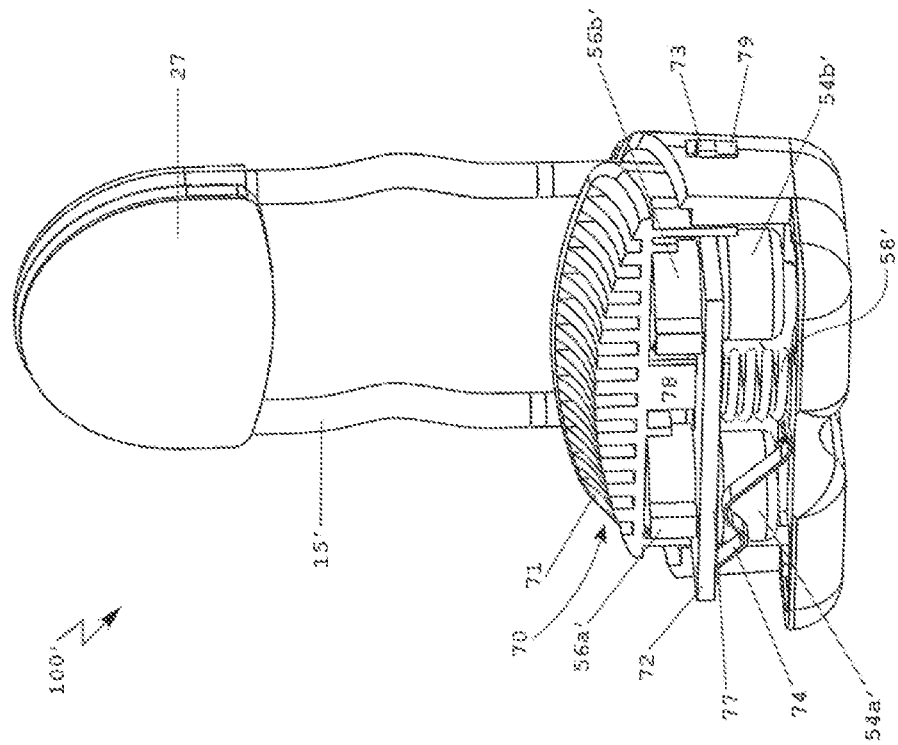
FIGS. 10A and 10B show, respectively, top perspective views of a cutaway view of a second device for collecting blood, in accordance with some embodiments of the present invention.
Figure 10B:
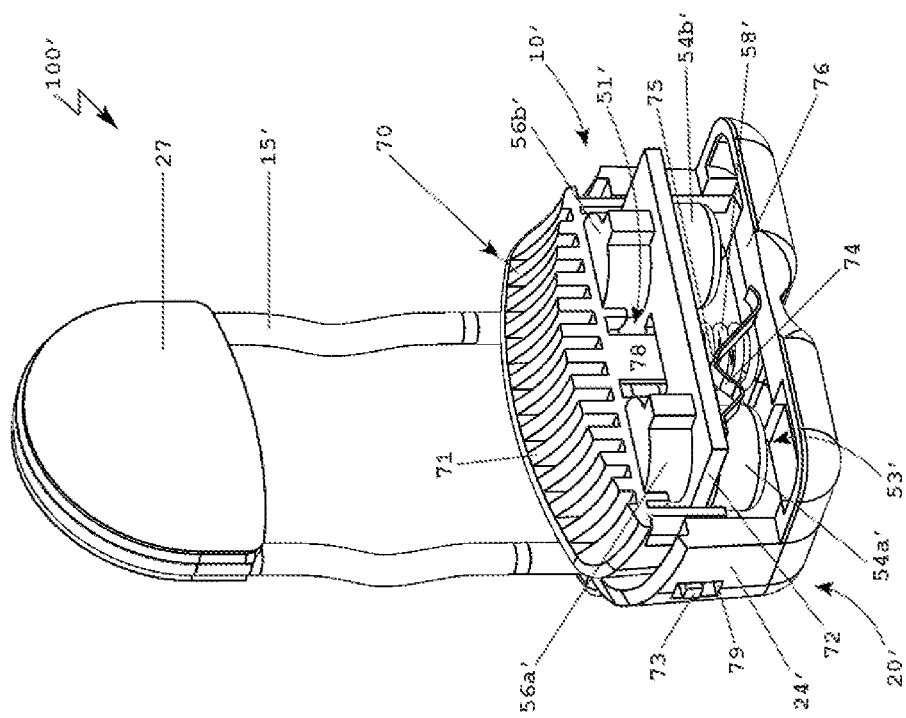
Figure 10C:
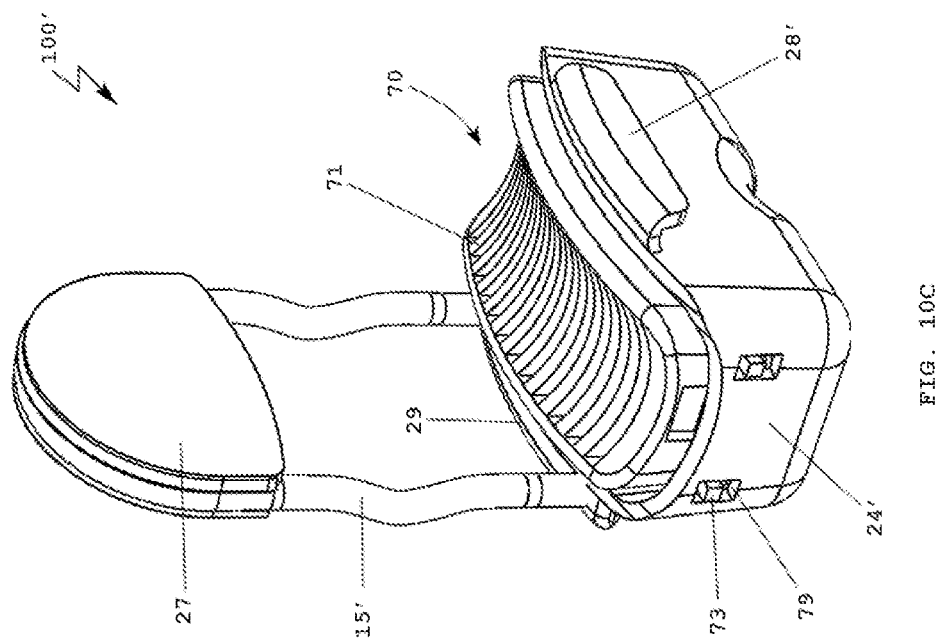
FIG. 10C shows a top perspective view of the second device of FIGS. 10A and 10B, in accordance with some embodiments of the present invention.
Figure 11A:
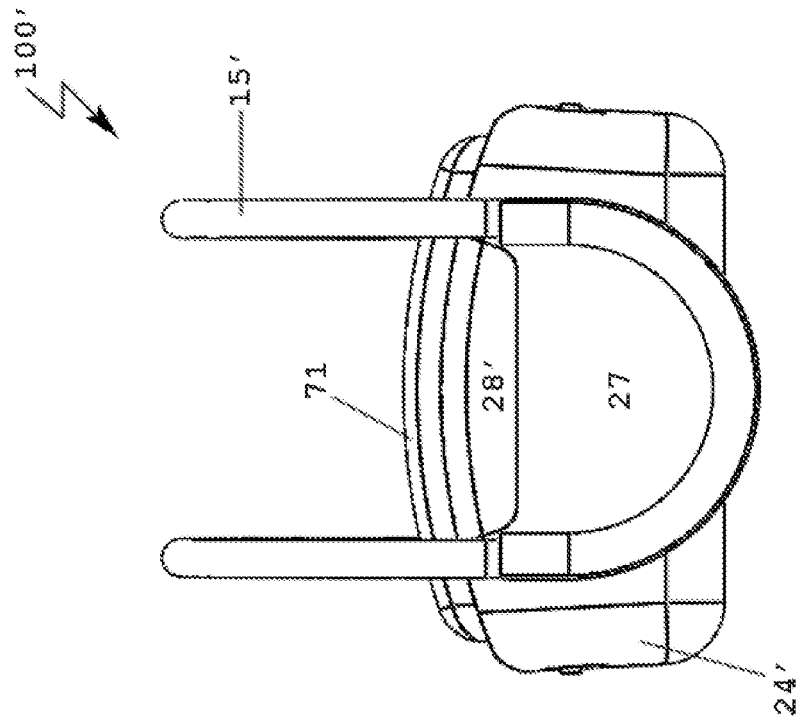
FIGS. 11A and 11B show side views of the second device of FIGS. 10A and 10B with the first biasing device attached to a lower portion, in accordance with some embodiments of the present invention.
Figure 11B:
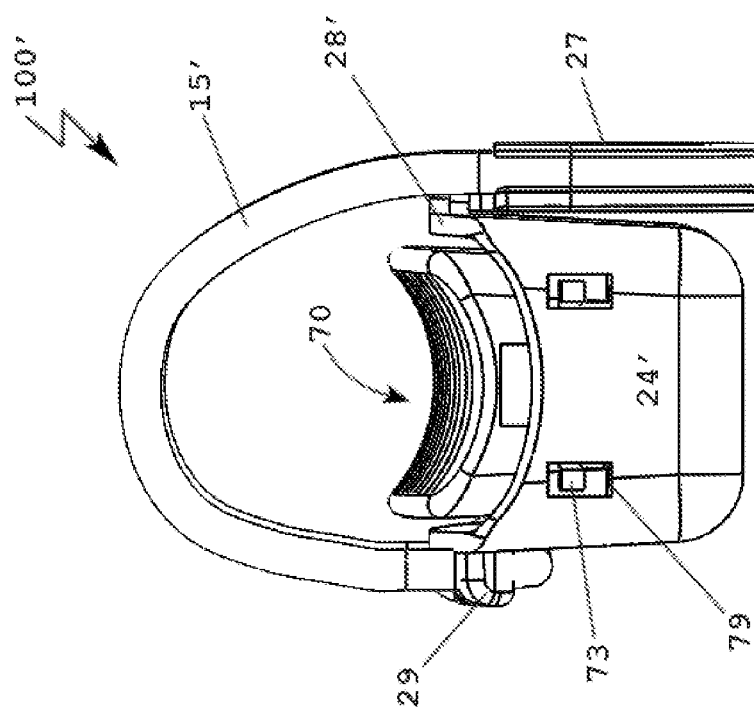
Figure 12:
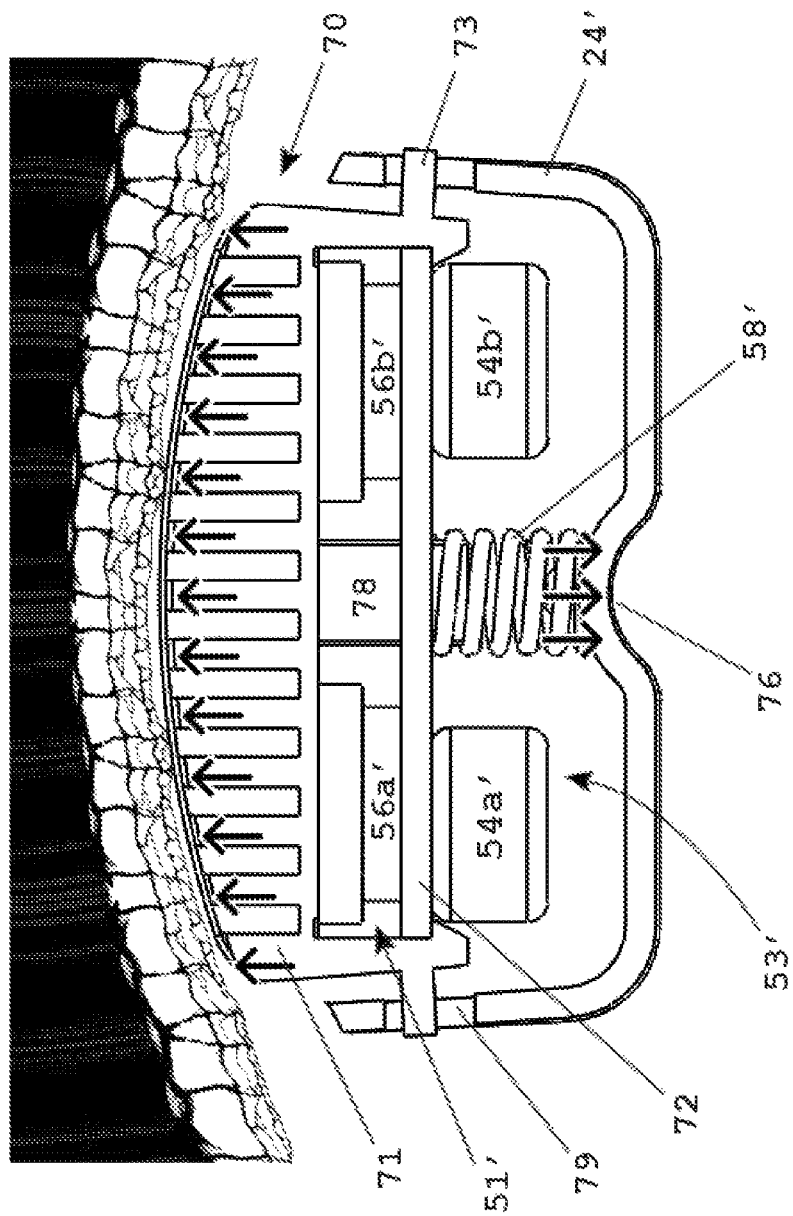
FIG. 12 shows a side cutaway view of the second device of FIGS. 10A through 10C in a compressed (ON) condition, in accordance with some embodiments of the present invention.

As shown in FIGS. 10A, 10B, and 12, in some embodiments, the upper portion 10' of the device 100' may include a plenum space 51' that is dimensioned, structured, and arranged to accommodate (e.g., house) a printed circuit board (PCB) 72 and a plurality of (e.g., two) vibrating motors 56a', 56b'. The PCB 72 may be removably supportable by a number of (e.g., four) snap fits that are formed in the structure of the vibrating plate assembly 70 for that purpose.

In some variations, the PCB 72 may include a processing device (e.g., a microprocessor unit) that is capable of executing a software program, algorithm, driver program, and the like stored in memory. In some embodiments, the software program, algorithm, driver program, and the like may be adapted to control the frequency and/or amplitude of the vibrations produced by each motor 56a', 56b', thereby defining the final beating frequency output. The PCB 72 may also include other hardware and/or software for driving the motors 56a', 56b', voltage regulators, and other circuit protection components on the PCB 72.

In some applications, the vibrating motors 56a', 56b' may be operatively positioned on a first side of the PCB 72, such that vibrating motors 56a', 56b' will physically contact the vibrating plate assembly 70 (when the vibrating plate assembly 70 is in a compressed (ON) state or condition). On the opposing (e.g., reverse) side of the PCB 72, a corresponding plurality of energy-producing or energy-storing devices (e.g., batteries) 54a', 54b' and a leaf spring mechanism 74 may be operatively positioned, such that each of the energy-producing or energy-storing devices (e.g., batteries) 54a', 54b' may be in electrical communication with a respective vibrating motor 56a', 56b', when the device 100' is in a compressed (ON) state or condition.

Preferably, the leaf spring mechanism 74 provides an S-shaped configuration, such that a first, proximal end of the leaf spring mechanism 74 is fixedly attached to a first electrical connection (e.g., an anode) disposed on the opposing (e.g., reverse) face of the PCB 72 and a second, distal end of the leaf spring mechanism 74 is unattached, hanging, and/or unsupported in free space. When the distal end of the leaf spring mechanism 74 is hanging in free space or, alternatively, in contact with a non-electrically conductive portion 76 of the lower portion 20' of the device 100', the device 100' is in an at-rest or OFF state or condition, as the leaf spring mechanism 74 provides an open circuit.

At an appropriate location, between the proximal and distal ends of the leaf spring mechanism 74, the leaf spring mechanism 74 may include a curved portion 75 that is structured and arranged, so that, when the device 100' is in an at-rest (OFF) state or condition, the curved portion 75 is unattached, hanging, and/or unsupported in free space; but that, when the device 100' is in a compressed (ON) state or condition—for example, when a (e.g. downward) force is applied to the vibrating plate assembly 70—the curved portion 75 is configured to contact a second electrical connection (e.g., a cathode 77) also located on the opposing (e.g., reverse) face of the PCB 72. Advantageously, the leaf spring mechanism 74 is manufactured from an electrically-conductive material (e.g., a conductive metal), so that when the curved portion 75 of the leaf spring mechanism 74 contacts the cathode 77, a closed circuit is created between the anode and the cathode 77, so that power from the energy-producing or energy-saving devices (e.g., batteries) 54a', 54b' may be provided or delivered to respective vibrating motors 56a', 56b'. Advantageously, when in a compressed state or condition, the closed circuit provides an auto-start capability to turn ON the device 100' without having to turn on the device 100' manually.

In some implementations, the upper portion 10' may also include: a plurality of quick connects 73 for releasably attaching the upper portion 10' to the lower portion 20' as well as a central post portion 78. In some applications, the quick connects 73 may be projections that are formed at both ends of the vibrating plate assembly 70, extending therefrom, for releasably connecting the upper portion 10' to the lower portion 20'. For example, each of the quick connects (i.e., projections) 73 may be adapted to fit into a corresponding opening 79 provided in the lower portion 20', so as to releasably connect the upper portion 10' to the lower portion 20'.

In some variations, the post portion 78 may be formed in the upper portion 10' of the device 100' (e.g., between the vibrating motors 56a', 56b') so as to be fixedly attached (e.g., at a proximal end of the post portion 78) to the vibrating plate assembly 70. In some implementations, the post portion 78 may extend through an opening in the PCB 72 formed for that purpose. Beneath the PCB 72, a (e.g., second) biasing member (e.g., a spring 58') may be disposed about (e.g., so as to be coaxial or concentric with) the post portion 78, such that a downward force applied to the vibrating plate assembly 70 (e.g., by a digit as shown in FIG. 12) will cause the PCB 72 to translate in the direction of the force and compress the spring 58'. As additional force is applied to the vibrating plate assembly 70, the PCB 72 compresses the spring 58', further compressing the leaf spring mechanism 74 between the PCB 72 and the non-electrically conductive portion 76 of the lower portion 20' of the device 100'. At some point during the compression, the curved portion 75 of the leaf spring mechanism 74 will contact the cathode 77, providing a closed circuit and turning ON the device 100'. Advantageously, when the second biasing 58' is not compressed, the second biasing device 58' may be structured and arranged to push (i.e., bias) the vibrating plate assembly 70 against the anatomical feature, so that the first 15' and second biasing devices 28' constrict blood flood to the capillaries in the anatomical feature contained in the device 100'.

In some embodiments, the lower portion 20' may include a housing portion 24'—manufactured, for example, from plastic, metal, and the like—that may include the non-electrically conductive portion 76 and that defines the limits and dimensions of a plenum space 53' provided inside of the housing portion 24'. In some implementations, the plenum space 53' may be dimensioned and configured to accommodate translation of the upper portion 10' when it is forced downwards, including the spring 58', the post portion 78, the PCB 72, the vibrating motors 56a', 56b', and the energy-producing or energy-saving devices (e.g., batteries) 54a', 54b'.

In operation, in order to maintain intimate contact between the digit or other portion of the human body and the vibrating plate assembly 70, a biasing element 15' (e.g., an elastic device, an elastic band, a rubber device, a rubber band, a hook and pile combination, and the like) may be removably and or partially fixedly attached to the lower portion 20' to hold the digit or other portion of the human body against the vibrating plate assembly 70. Advantageously, the biasing element 15' and lower portion 20' are further adapted to constrict the flow of blood to the digit or other portion of the human body. For example, in some embodiments, the biasing element 15'—or, alternatively, a pull tab 27 attached to a loop in the biasing element 15'—may be looped around attachment portions 28' formed on both sides of the housing portion 20' for the purpose of placing the biasing element 15' in tension. Alternatively, as shown in FIG. 10B, an attachment portion 28' may be formed on one side of the housing portion 20', while the other loop of the biasing element 15' may be restrained by a restraining device 29 on the other side of the housing portion 20'.

Although the figures show an embodiment that includes two motors 56a', 56b', this is done for illustrative purposes only. Performance may further be improved by using more than two motors 56a', 56b' to enhance the beating effect. In some instances, it may also be possible to produce a desired beating phenomenon use a single motor having a mechanism coupled to the motor's shaft. Such an arrangement would work more like a car's gearbox, which increases or reduced the output speed and torque mechanically rather than electronically.

Method of Drawing Blood

Figure 7:
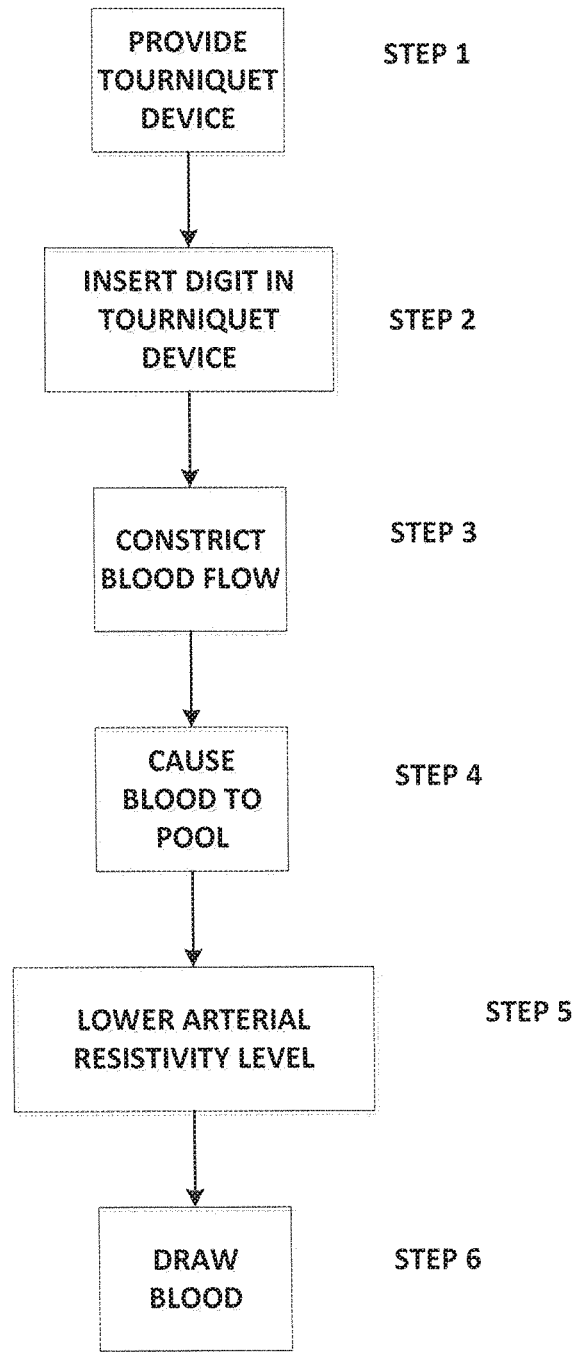
FIG. 7 shows a flow chart of a method of drawing blood, in accordance with some embodiments of the present invention.

Having described a device for use in collecting or drawing capillary blood from a fingertip of a mammalian subject, a method of drawing blood using the device will now be described. Referring to FIG. 7, in some embodiments, a method of drawing capillary blood from the fingertip of a mammalian subject may include promoting blood to pool proximate to or in the vicinity of the drawing site and, moreover, encouraging the pooled blood to flow into the capillaries from which the blood sample will be taken or drawn. Promoting blood to pool proximate to or in the vicinity of the drawing site can include, for example, constricting blood flow in the digit, while encouraging the pooled blood to flow into the capillaries may involve lowering the arterial resistivity index. The previously described device provides each of these desirable qualities.

Accordingly, in a first step, a tourniquet device similar to the one previously described may be provided (STEP 1) and the digit, from whence the capillary blood sample will be drawn, maybe placed in the tourniquet device (STEP 2).

Figure 8:
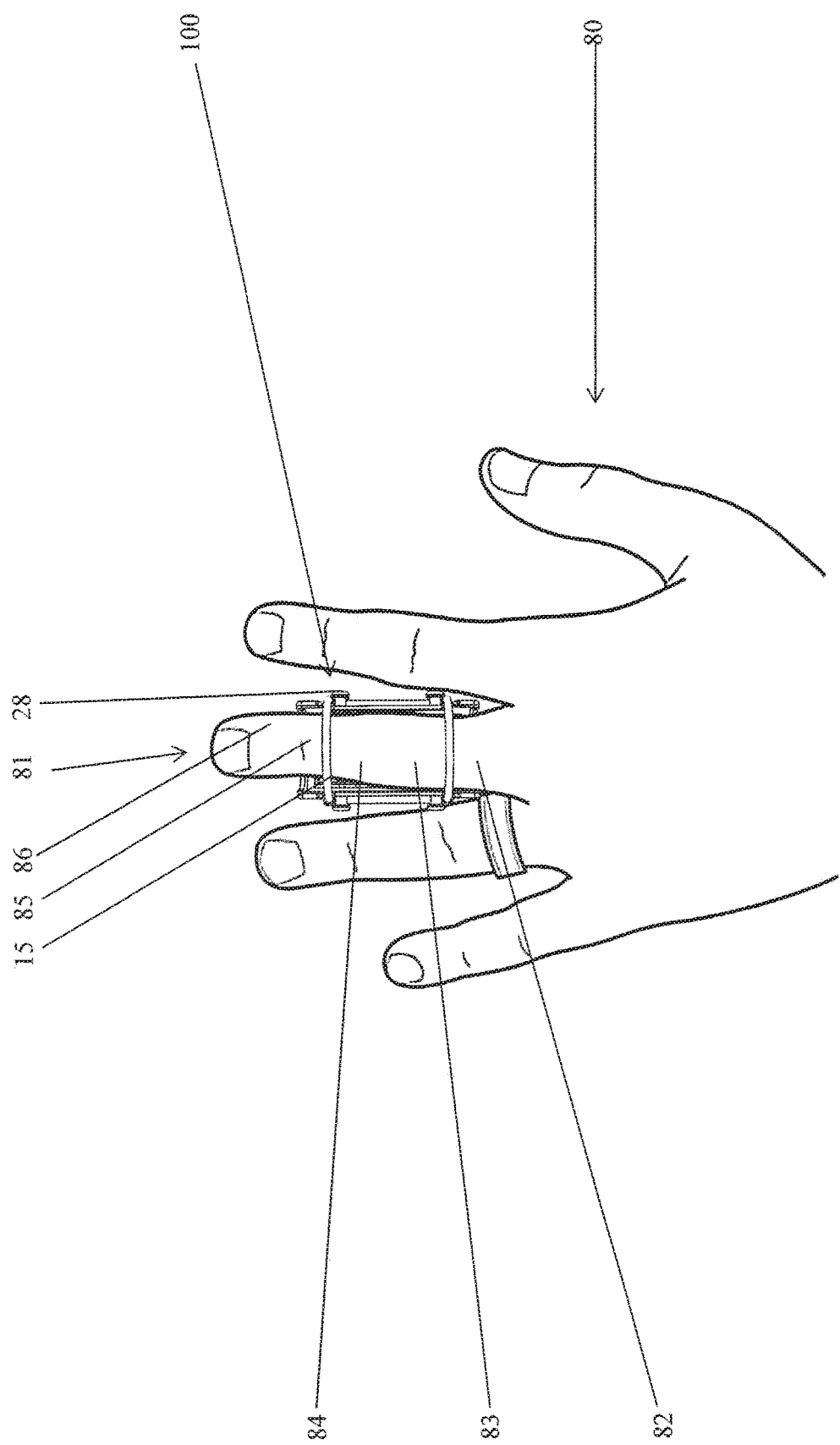
FIG. 8 shows a middle finger inserted in the device of FIG. 1, in accordance with some embodiments of the present invention.

For example, FIG. 8 shows a tourniquet device 100 disposed on the middle finger 81 of a subject's left hand 80. In particular, the proximal 82 and middle phalanxes 84 of the subject's middle finger 81 may be placed in the cradle portion 10 of the device 100 (STEP 2), such that the proximal interphalangeal joint 83 is resting on some portion of the extended rib portion 13. The distal phalanx 86 and distal interphalangeal joint 85 may be substantially out of the cradle portion 10 of the device 100. The biasing element 15 may then be stretched over each of the attachments posts 28, so that the tension in the biasing element 15 restricts (i.e., constricts or partially blocks) blood flow in the middle finger 81 (STEP 3).

More specifically, the rigid ribbed, vibrating plate 11 on which the finger 81 is placed and the more elastic biasing element 15 across the top of the finger 81 constrict or partially block the flow of blood out of the finger 81 without completely cutting off blood supply to the finger 81. Due to the higher arterial blood pressure relative to the lower venous blood pressure and the constriction afforded by the biasing element 15, the rate at which blood enters the finger 81 exceeds the rate at which blood exits the finger 81, causing blood to pool in the finger 81 proximate or in the vicinity of, for example, the distal phalanx 86.

Capillaries are extremely tiny blood vessels. However, low frequency vibrations have been used to promote dilation in capillaries, resulting in more red blood cells entering the capillaries. Furthermore, vibrations that have low frequency and high amplitude typically increase the deformability of the cell walls of red blood cells, making it easier for blood cells to squeeze into a tiny capillary. Accordingly, subjecting the pooling blood to low frequency and/or high amplitude vibrations promotes greater blood flow (STEP 5) into the dilated capillaries. Indeed, vibrations that have a low frequency and/or a high amplitude lower the arterial resistivity index, i.e., the resistive force that a microvascular bed applies to the blood which is flowing through it, making it easier for blood to flow to areas of the body where there is less blood supply. Low frequency vibrations also cause vasodilation, i.e., a widening of the blood vessels.

In some instances, creating low frequency vibrations is simple, especially using large mechanical devices, such as gearboxes, levers, shafts, and so forth. In small, compact devices, however, such mechanical systems cannot be used because of lack of space, weight restriction, and/or associated costs. Thus, beating phenomenon (also known as beating frequency or simply beats) may be employed to combine multiple (e.g., two) high frequency (e.g., vibratory) waves to create a resultant low frequency output. The phenomena by which two high frequencies (e.g. vibratory) waves enforce each other or cancel out each other are referred to, respectively, as constructive interference and destructive interference, which is shown in FIG. 9.

Figure 9:
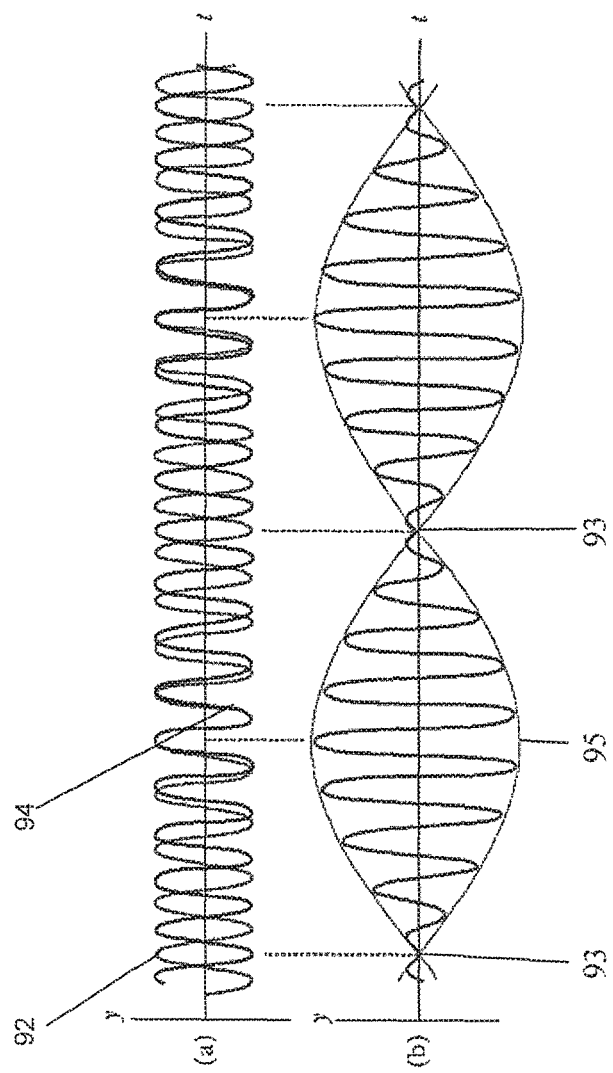
FIG. 9 shows constructive and destructive interference of a vibratory wave, in accordance with some embodiments of the present invention.

The upper displacement versus time relationship (labeled (a)) in FIG. 9 shows two high frequency (e.g., vibratory) waves 92, 94 being overlapped on each other. Typical waves 92, 94 generated by small vibratory motors may be characterized as having slightly different (high) frequencies but having the same or substantially the same relatively high amplitudes. As shown in the lower relationship (labeled (b)) in FIG. 9, at certain instances 93, when the two relatively high amplitude, high frequency waves 92, 94 are combined, e.g., by a processing device, the resultant wave may be characterized as a high amplitude, low frequency wave. Indeed, in some implementations, the processing device may be adapted to combined two waves 92, 94, such that, in the resultant wave, at certain instances 93, the combined waves 92, 94 cancel each other out, while at other instances 95, the combined waves 92, 94 enforce each other. The net effect of this constructive and destructive interference results in a high amplitude, low frequency wave. In short, the beating phenomenon enables a transfer of energy into the system where low-frequency vibrations can be induced by coupling vibrations from multiple (e.g., two) high-frequency sources.

With a sufficient supply of blood in the fingertip, after lancing, an ample amount of blood may be collected (STEP 6) using techniques that are well known to the art.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What we claim is:

1. A device for collecting blood from an anatomical feature of a mammalian subject, the device comprising:
    a vibrating plate assembly structured and arranged to be in contact with the anatomical feature from which blood is collected;
    a housing portion connected to the vibrating plate assembly;
    a first biasing device attached to the housing portion and releasably attachable to the vibrating plate assembly, wherein the first biasing device is structured and arranged to constrict blood flow in the anatomical feature;
    a second biasing device disposed between the housing portion and the vibrating plate assembly; and
    a plurality of vibrating motors located beneath the vibrating plate assembly, wherein vibrations generated by the vibrating motors are configured to enhance blood flow in and to the anatomical feature, wherein the second biasing device is one or both of:
        (i) structured and arranged to bias the vibrating plate assembly against the anatomical feature, and
        (ii) structured and arranged to bias the vibrating motors against the vibrating plate assembly.

2. The device of claim 1, wherein the vibrating plate assembly comprises a plurality of ribs.

3. The device of claim 1, wherein the first biasing device is selected from the group consisting of an elastic device, an elastic band, a rubber device, and a rubber band.

4. The device of claim 1, wherein the first biasing device comprises a hook and pile combination.

5. The device of claim 1, further comprising at least one power source.

6. The device of claim 5, wherein the power source is a battery.

7. The device of claim 1, further comprising:
    a post portion fixedly attached to the vibrating plate assembly, wherein the second biasing device is disposed about the post portion.

8. The device of claim 7, wherein the second biasing device comprises a spring.

9. The device of claim 1, further comprising a leaf spring mechanism that is structured and arranged to provide an auto-start condition when the leaf spring mechanism is compressed.

10. The device of claim 1, wherein the first biasing device comprises a pull tab.

11. The device of claim 1, wherein the vibrating plate assembly comprises a plurality of quick connect projections for releasably attaching the vibrating plate assembly to the housing portion.

12. The device of claim 11, wherein the quick connect projections are configured to mate with corresponding openings formed in the housing portion.

13. The device of claim 1, further comprising a printed circuit board that is releasably attachable to the vibrating plate assembly.

14. The device of claim 13, wherein the printed circuit board comprises an opening through which a post portion extends.

15. The device of claim 13, wherein a leaf spring mechanism for placing the device in an ON state is fixedly attached to a bottom surface of the printed circuit board.

16. The device of claim 15, wherein the leaf spring mechanism comprises an S-shaped mechanism.

17. A method of collecting capillary blood from an anatomical feature of a mammalian subject, the method comprising:
 providing a tourniquet device to constrict blood flow in the anatomical feature, the tourniquet device further comprising:
  a vibrating plate assembly structured and arranged to be in contact with the anatomical feature from which blood is collected;
  a housing portion connected to the vibrating plate assembly;
  a first biasing device attached to the housing portion and releasably attachable to the vibrating plate assembly, wherein the first biasing device is structured and arranged to constrict blood flow in the anatomical feature;
  a second biasing device disposed between the housing portion and the vibrating plate assembly; and
  a plurality of vibrating motors located beneath the vibrating plate assembly, wherein vibrations generated by the vibrating motors are configured to enhance blood flow in and to the anatomical feature, wherein the second biasing device is one or both of:
   (i) structured and arranged to bias the vibrating plate assembly against the anatomical feature, and
   (ii) structured and arranged to bias the vibrating motors against the vibrating plate assembly;
 positioning the first biasing device over the anatomical feature retained in the vibrating plate assembly;
 releasably attaching the first biasing device to the vibrating plate assembly to constrict blood flow in the anatomical feature; and
 producing vibrations by the vibrating motors, such that the vibrations are configured to translate to the anatomical feature retained in the vibrating plate assembly, thereby increasing blood flow into the capillaries in the anatomical feature for collection.

18. The method of claim 17, wherein the second biasing device is attached to the housing portion and is releasably attachable to the vibrating plate assembly, and wherein the second biasing device is structured and arranged to push the vibrating plate assembly against the anatomical feature.

* * * * *